United States Patent [19]

Rubinfeld

[11] Patent Number: 5,199,445
[45] Date of Patent: Apr. 6, 1993

[54] STROMAL PUNCTURE METHOD
[75] Inventor: Roy S. Rubinfeld, Bethesda, Md.
[73] Assignee: Look, Inc., Norwell, Mass.
[21] Appl. No.: 787,799
[22] Filed: Nov. 4, 1991

Related U.S. Application Data

[62] Division of Ser. No. 533,923, Jun. 6, 1990, abandoned.
[51] Int. Cl.[5] ............................................. A61B 17/34
[52] U.S. Cl. ................................... 128/898; 606/166; 606/185
[58] Field of Search ..................... 606/166, 185, 181; 128/898

[56] References Cited

PUBLICATIONS

McLean et al., Ophthalmology 93:784–788, 1986.
Visitec Catalog, pp. 2, 3, 4, 5 and 7, 1987.
Anterior Stromal Puncture for Recurrent Erosion: Further Experience and New Instrumentation; Ophthalmocare Surgery-May 1990, vol. 21, No. 5.
Rubinfeld, "Anterior Stromal Puncture for Recurrent Erosion: Further Experience and New Instrumentation", Ophthalmic Surgery, vol. 21, No. 5, May 1990.
Rubinfeld, "Successful Treatment of Recurrent Corneal Erosion With Nd:YAG Anterior Stromal Puncture", American Journal of Opthalmology, vol. 111, No. 2, Feb. 1991.
Katsev, et al., "Recurrent Corneal Erosion:Pathology of Corneal Puncture", Cornea, vol. 10, No. 5, 1991.
Look, Inc.–Look Disposable Ophthalmic Instruments–Brochure.
Wood & McLaughlin–Recurrent Erosion–International Ophthalmology Clinics–Spring 1988.

Primary Examiner—Michael H. Thaler
Attorney, Agent, or Firm—Cushman, Darby & Cushman

[57] ABSTRACT

A corneal stromal puncture needle for ophthalmic surgery having a cutting tip from 0.1 to 0.6 mm in length extending from the needle shaft at an included angle of 75° to 105°.

4 Claims, 1 Drawing Sheet

STROMAL PUNCTURE METHOD

This is a division of application Ser. No. 06/533,923, filed Jun. 6, 1990, now abandoned.

This invention relates to a stromal puncture needle for use in ophthalmic surgery.

BACKGROUND OF THE INVENTION

Anterior stromal puncture has been proposed as a treatment for recalcitrant cases of recurrent corneal erosion by McLean et al., Ophthalmol., Vol. 93, 784-788 (1986). However, the surgical instruments available have been designed for use in quite different procedures and are not well suited for use in stromal puncture. Attempts to use both cystotomes and straight needles, e.g., tuberculin needles for stromal puncture have shown them to be difficult to use safely and to involve the risk of corneal perforation and possibly excessive scarring.

The present invention provides a stromal puncture needle of unique design which can readily be used by any ophthalmic surgeon, and the use of which is substantially free from the risk of corneal perforation. By the use of this invention scarring is also minimized.

In general, the needle of the invention comprises a conventional needle hub which serves for mounting the needle on any suitable handle. Fixed to and extending from the hub is a generally straight portion of a needle shaft from 19 to 31 gauge, preferably about 25 gauge. The length of the straight portion is not critical and at its end distal from the hub the shaft is bent through an angle of 35°-155° to provide a generally straight extension having at its distal end a cutting tip forming an included angle of 75°-105° with the extension and lying in the same plane as that defined by the straight portion and the extension of the shaft. The tip lies on the same side of the extension as the convex side of the bend in the shaft and has a length of 0.1 to 0.6 mm measured from the adjacent side of the extension.

The needle may also be said to comprise a hub and a generally Z-shaped shaft having a proximal leg, an intermediate leg and a distal leg lying generally in a single plane with the proximal leg secured to and extending from the hub. The distal leg and intermediate leg are connected by a bend forming an included angle from 135° to 155°; the length of the intermediate leg may vary from 10 to 30 mm. The distal leg, which extends toward the axis of the proximal leg terminates in a sharpened cutting point or edge. The length of the distal leg is 0.1 to 0.6 mm measured from the adjacent side of the intermediate leg to the end of the cutting point, and the distal leg is approximately perpendicular to the intermediate leg. That is, the included angle between the intermediate leg and the distal leg is 75°-105°.

IN THE DRAWING

Figure 1:
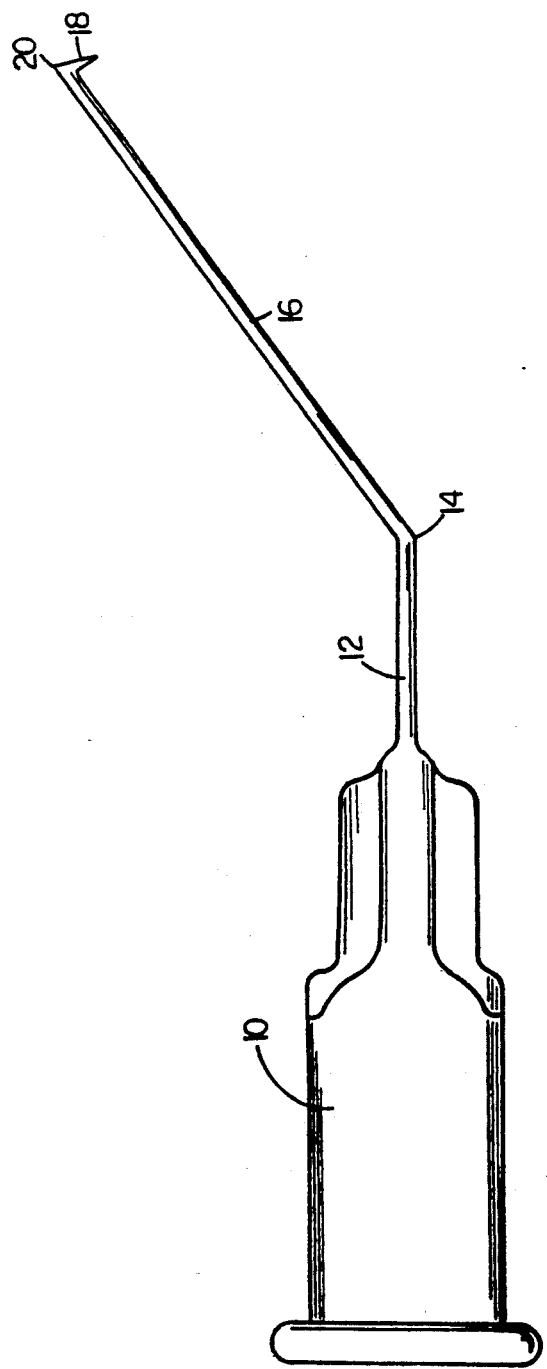
FIG. 1 is a view in side elevation of one embodiment of the invention.
Figure 2:
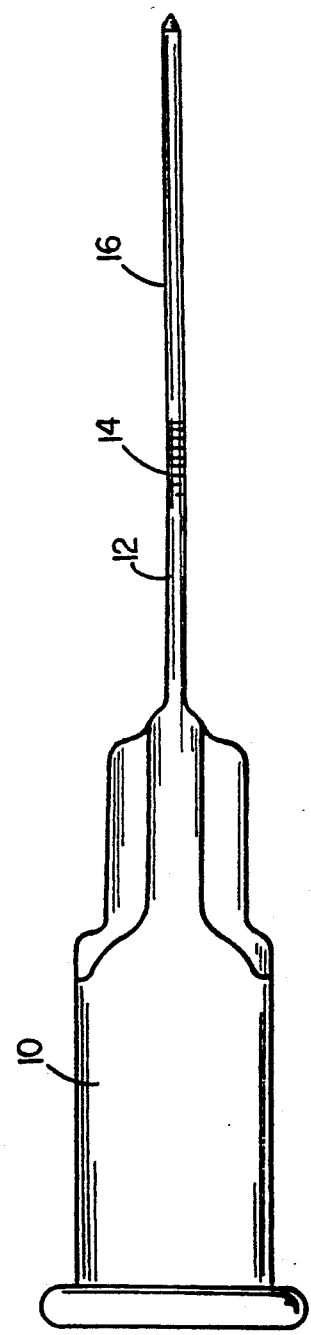
FIG. 2 is a top view.

The needle of the invention comprises a hub 10, which in a preferred embodiment is a standard polypropylene Luer Lock hub, together with a 25 -b 51996775.001 gauge cannula of shaft 12 projecting axially from the hub for a distance of 5-10 mm. The cannula or shaft 12 is bent at an angle 14 of approximately 145° to provide an extended segment 16 which is approximately 18 mm in length. The extended segment 16 carries at its outer end a cutting tip 18 formed by a retrograde bend 20 extending toward the axis of shaft 12 and terminating in a sharpened cutting point. The length of tip 18, measured from the nearest surface of segment 16 to the end of the sharpened point is from 0.1 to 0.6 mm, preferably about 0.25 mm. The included angle formed by segment 16 and tip 18 is approximately 90°, so that tip 18 is approximately perpendicular to the axis of segment 16.

Cannula or shaft 12 together with extension segment 16 and cutting tip 18 may be solid or hollow, as desired. The hub 10 may be mounted on any desired handle prior to use.

In use, the extension segment 16 is held so that it is approximately tangential to the corneal surface at the point of contact between cutting tip 18 and the anterior surface of the cornea. The needle as a whole is then advanced toward the eyeball. Depth of penetration of tip 18 is limited to the distance between the sharpened point and the nearest surface of segment 16, the latter serving as a stop when it contacts the surface of the cornea, thus preventing corneal perforation and limiting scarring.

What is claimed is:

1. A method of performing anterior stromal puncture on a portion of the anterior surface of the cornea of an eyeball comprising:

a) providing a stromal puncture needle having a proximal portion, an intermediate portion, and a distal portion, each of said portions having a proximal end and a distal end and a longitudinal axis extending therebetween; said intermediate portion extending from said proximal portion so that said longitudinal axis of said intermediate portion describes an angle of between 135° and 155° with said longitudinal axis of said proximal portion; said distal portion extending from said distal end of said intermediate portion so that said longitudinal axis of said distal portion describes an angle of between 75° and 105° with said longitudinal axis of said intermediate portion; said proximal portion, said intermediate portion and said distal portion being defined in a single plane; said proximal portion and said intermediate portion being 25 gauge and said intermediate portion having a length of about 18 mm; said distal portion defining a cutting tip which terminates distally in a piercing point; said distal portion having a length of between 0.1 mm and 0.25 mm;

b) holding said stromal puncture needle so that said intermediate portion is approximately tangential to a point of contact between said piercing point and the anterior surface of the cornea;

c) advancing said stromal puncture needle towards the anterior surface of the cornea thereby to insert distal portion into the stroma to a depth defined by said maximum length of said distal portion and at most until said intermediate portion contacts the anterior surface of the cornea thereby to limit said penetration of said distal portion;

d) withdrawing said stromal puncture needle from the stroma; and e) repeating steps c) and d) a plurality of times thereby to form a plurality of punctures of limited depth in the anterior surface of the cornea.

2. A method as in claim 1, wherein said step of providing a stromal puncture needle comprises providing a stromal puncture needle which is solid.

3. A method as in claim 1, wherein said step of providing comprises providing a distal portion which describes an angle of about 90° with respect to the intermediate portion.

4. A method as in claim 1, wherein said step of providing comprises providing a distal portion having a length of about 0.25 mm.

* * * * *